US012127760B2

United States Patent
Madan et al.

(10) Patent No.: US 12,127,760 B2
(45) Date of Patent: Oct. 29, 2024

(54) SURGICAL INSTRUMENT WITH VARIABLE CLAMPING FORCE

(71) Applicant: Cilag GmbH International, Zug (CH)

(72) Inventors: Ashvani K. Madan, Mason, OH (US); David C. Groene, Cincinnati, OH (US); Benjamin M. Boyd, Fairborn, OH (US); Craig N. Faller, Batavia, OH (US); Jacob S. Gee, Cincinnati, OH (US); Paul F. Riestenberg, North Bend, OH (US)

(73) Assignee: Cilag GmbH International, Zug (CH)

( * ) Notice: Subject to any disclaimer, the term of this patent is extended or adjusted under 35 U.S.C. 154(b) by 792 days.

(21) Appl. No.: 17/191,832

(22) Filed: Mar. 4, 2021

(65) Prior Publication Data

US 2021/0259724 A1   Aug. 26, 2021

Related U.S. Application Data

(63) Continuation of application No. 16/280,309, filed on Feb. 20, 2019, now Pat. No. 10,973,541, which is a
(Continued)

(51) Int. Cl.
*A61B 17/32* (2006.01)
*A61B 17/00* (2006.01)
*A61B 17/295* (2006.01)

(52) U.S. Cl.
CPC .... *A61B 17/320068* (2013.01); *A61B 17/295* (2013.01); *A61B 17/320092* (2013.01);
(Continued)

(58) Field of Classification Search
CPC .......... A61B 17/320068; A61B 17/295; A61B 17/320092; A61B 2017/00017; A61B 2017/00022; A61B 2017/0011
See application file for complete search history.

(56) References Cited

U.S. PATENT DOCUMENTS 5,322,055 A   6/1994   Davison et al.
5,324,299 A   6/1994   Davison et al.
(Continued)

FOREIGN PATENT DOCUMENTS

CN   101401736 A   4/2009
CN   102665575 A   9/2010
(Continued)

OTHER PUBLICATIONS

Brazil Office Action dated Jun. 18, 2020, for Application No. BR112018012567-9, 4 pages.
(Continued)

*Primary Examiner* — Sarah A Long
*Assistant Examiner* — James R McGinnity
(74) *Attorney, Agent, or Firm* — Frost Brown Todd LLP

(57) ABSTRACT

An ultrasonic instrument includes a body and a shaft assembly extending distally from the body. The shaft assembly includes an acoustic waveguide. The instrument further includes an end effector including an ultrasonic blade. The ultrasonic blade is in acoustic communication with the acoustic waveguide. The instrument further includes a sensor configured to sense at least one characteristic of the shaft assembly and/or the end effector. The end effector is configured to be activated at varying power levels based on the at least one characteristic sensed by the sensor.

16 Claims, 6 Drawing Sheets

Related U.S. Application Data continuation of application No. 14/976,087, filed on Dec. 21, 2015, now Pat. No. 10,368,894.

(52) U.S. Cl.
CPC ............... *A61B 2017/00017* (2013.01); *A61B 2017/00022* (2013.01); *A61B 2017/0011* (2013.01); *A61B 2017/320071* (2017.08); *A61B 2017/320094* (2017.08); *A61B 2017/320095* (2017.08)

(56) References Cited

U.S. PATENT DOCUMENTS

| | | | |
|---|---|---|---|
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,468,454 B2 | 10/2016 | Johnson et al. | |
| 10,368,894 B2 | 8/2019 | Madan et al. | |
| 10,973,541 B2 | 4/2021 | Madan et al. | |
| 2006/0079874 A1 | 4/2006 | Faller et al. | |
| 2007/0011713 A1 | 1/2007 | Abramson et al. | |
| 2007/0191713 A1 | 8/2007 | Eichmann et al. | |
| 2007/0282333 A1 | 12/2007 | Fortson et al. | |
| 2008/0009860 A1 | 1/2008 | Odom | |
| 2008/0200940 A1 | 8/2008 | Eichmann et al. | |
| 2012/0112687 A1 | 5/2012 | Houser et al. | |
| 2012/0116265 A1 | 5/2012 | Houser et al. | |
| 2013/0121366 A1 | 5/2013 | Misuchenko et al. | |
| 2013/0324991 A1 | 12/2013 | Clem et al. | |
| 2014/0005701 A1 | 1/2014 | Olson et al. | |
| 2014/0114334 A1* | 4/2014 | Olson | A61B 34/37 606/169 |
| 2015/0080924 A1 | 3/2015 | Stulen et al. | |
| 2015/0209061 A1 | 7/2015 | Johnson et al. | |
| 2018/0199958 A1* | 7/2018 | Beaupré | A61B 17/320092 |

FOREIGN PATENT DOCUMENTS

| | | |
|---|---|---|
| CN | 103281983 A | 9/2013 |
| CN | 104582627 A | 4/2015 |
| EP | 2772206 A2 | 9/2014 |
| JP | 2001-346806 A | 12/2001 |
| JP | 2007-275291 A | 10/2007 |

OTHER PUBLICATIONS

Chinese Office Action, The First Office Action, and First Search, dated Jun. 30, 2020, for Application No. 201680074934.7, 13 pages.
Chinese Office Action, Notification of Second Office Action, dated Dec. 30, 2020, for Application No. 2016800749347, 5 pages.
European Communication dated Apr. 23, 2021, for Application No. 16828821.5, 5 pages.
International Search Report and Written Opinion dated Apr. 19, 2017, for International Application No. PCT/US2016/066465, 11 pages.
Japanese Office Action, Notice of Reasons for Refusal, and Search Report by Registered Search Organization dated Jan. 19, 2021, for Application No. 2018-550658, 42 pages.
Mexican Office Action dated Sep. 10, 2020, for Application No. MX/a/2018/007617, 3 pages.
U.S. Appl. No. 61/410,603, entitled "Energy-Based Surgical Instruments," filed Nov. 5, 2010.

* cited by examiner

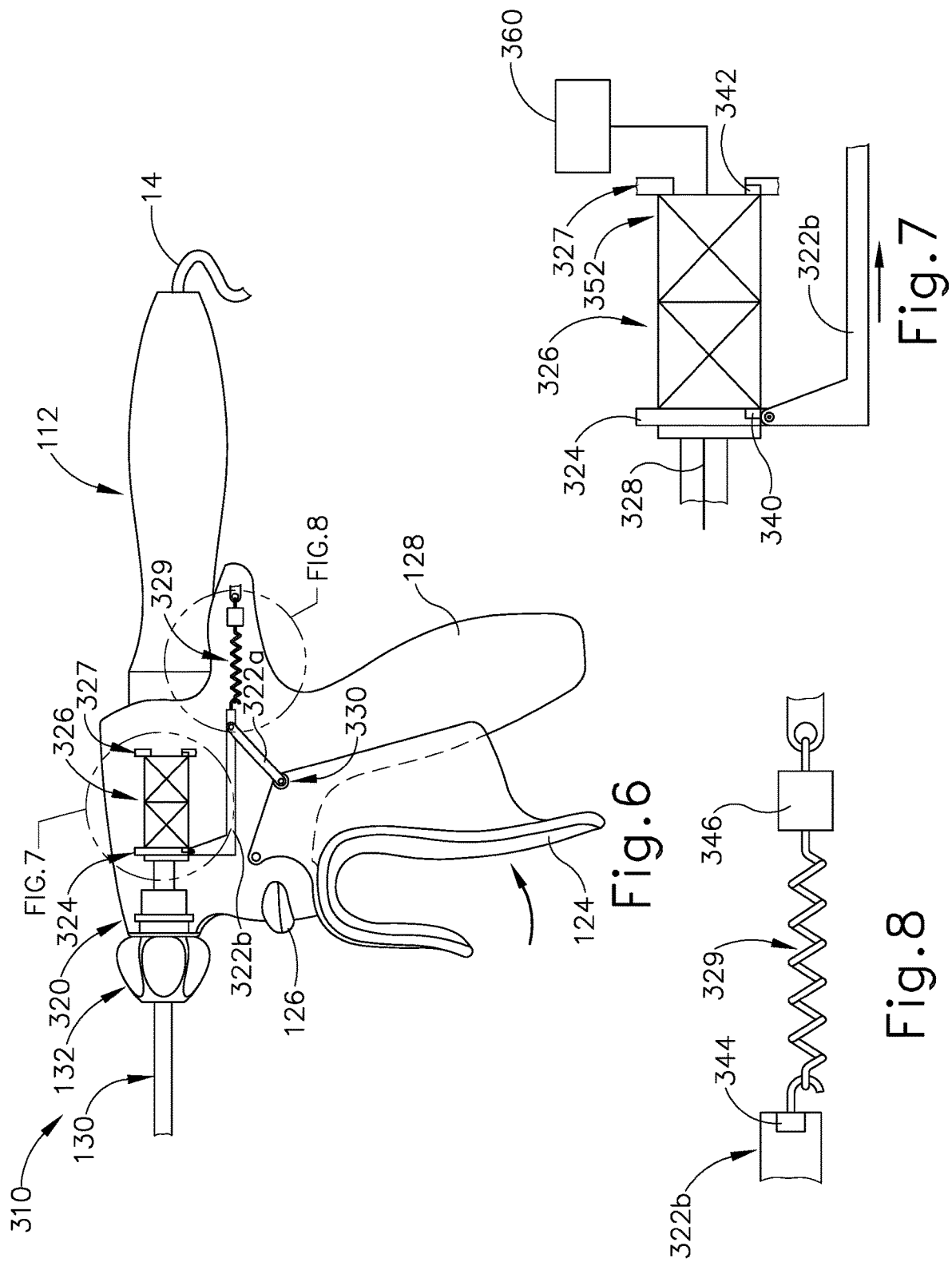

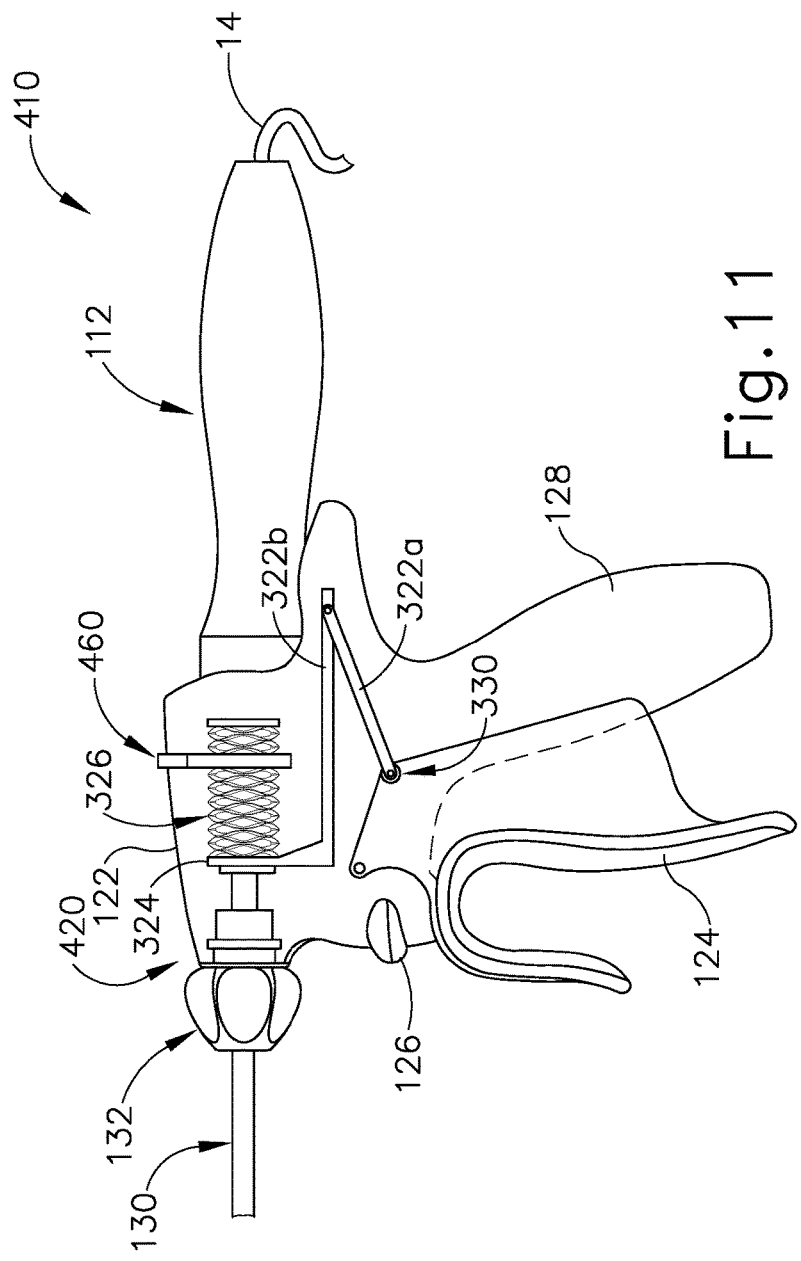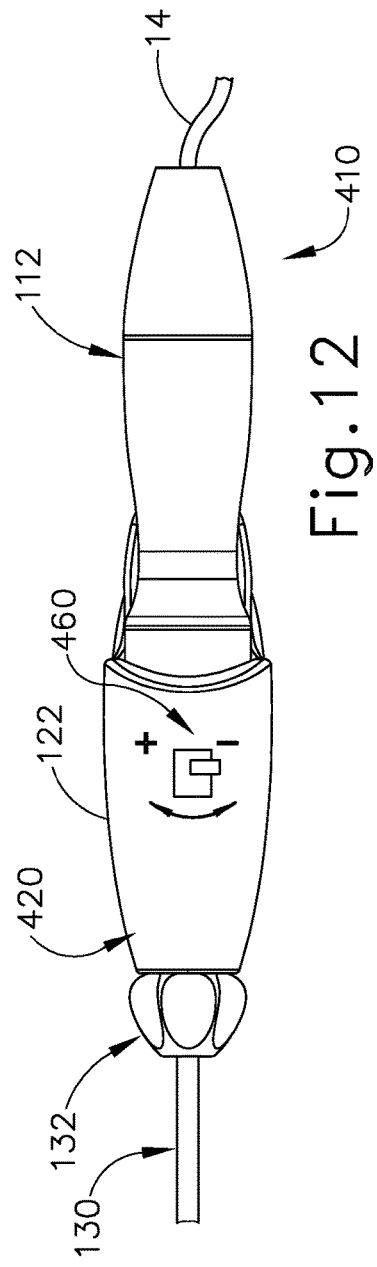

SURGICAL INSTRUMENT WITH VARIABLE CLAMPING FORCE

This application is a continuation of U.S. patent application Ser. No. 16/280,309, entitled "Surgical Instrument with Variable Clamping Force," filed Feb. 20, 2019 and issued as U.S. Pat. No. 10,973,541 on Apr. 13, 2021, which is a continuation of U.S. patent application Ser. No. 14/976,087, entitled "Surgical Instrument with Variable Clamping Force," filed Dec. 21, 2015 and issued as U.S. Pat. No. 10,368,894 on Aug. 6, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACER Ultrasonic Shears, the HARMONIC WAVER Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a side elevational view of an another exemplary alternative form that an instrument of the system of FIG. 1 may take;

FIG. 7 depicts a schematic view of a first set of internal components of the instrument of FIG. 6;

FIG. 8 depicts a schematic view of a second set of internal components of the instrument of FIG. 6;

FIG. 11 depicts a side elevational view of an another exemplary alternative form that an instrument of the system of FIG. 1 may take; and FIG. 12 depicts a top elevational view of the instrument of FIG. 11.

Figure 1:
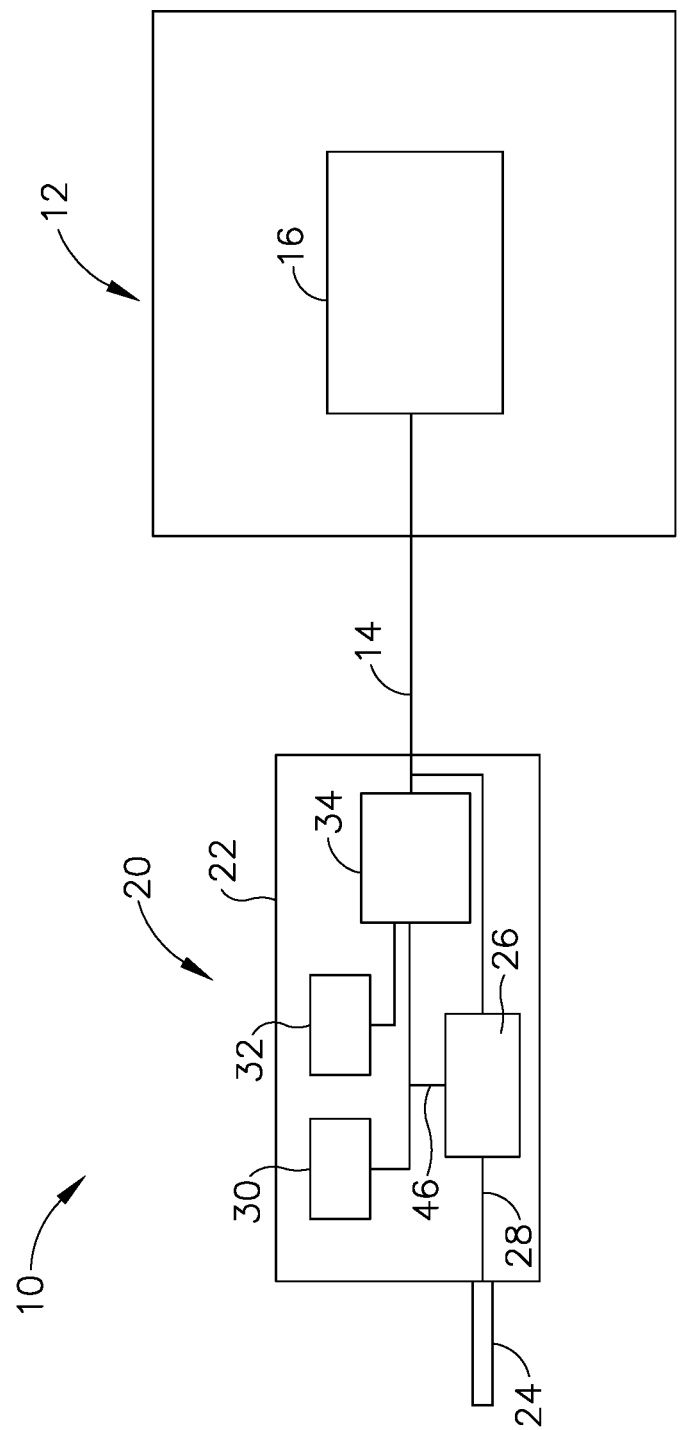
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (n)/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
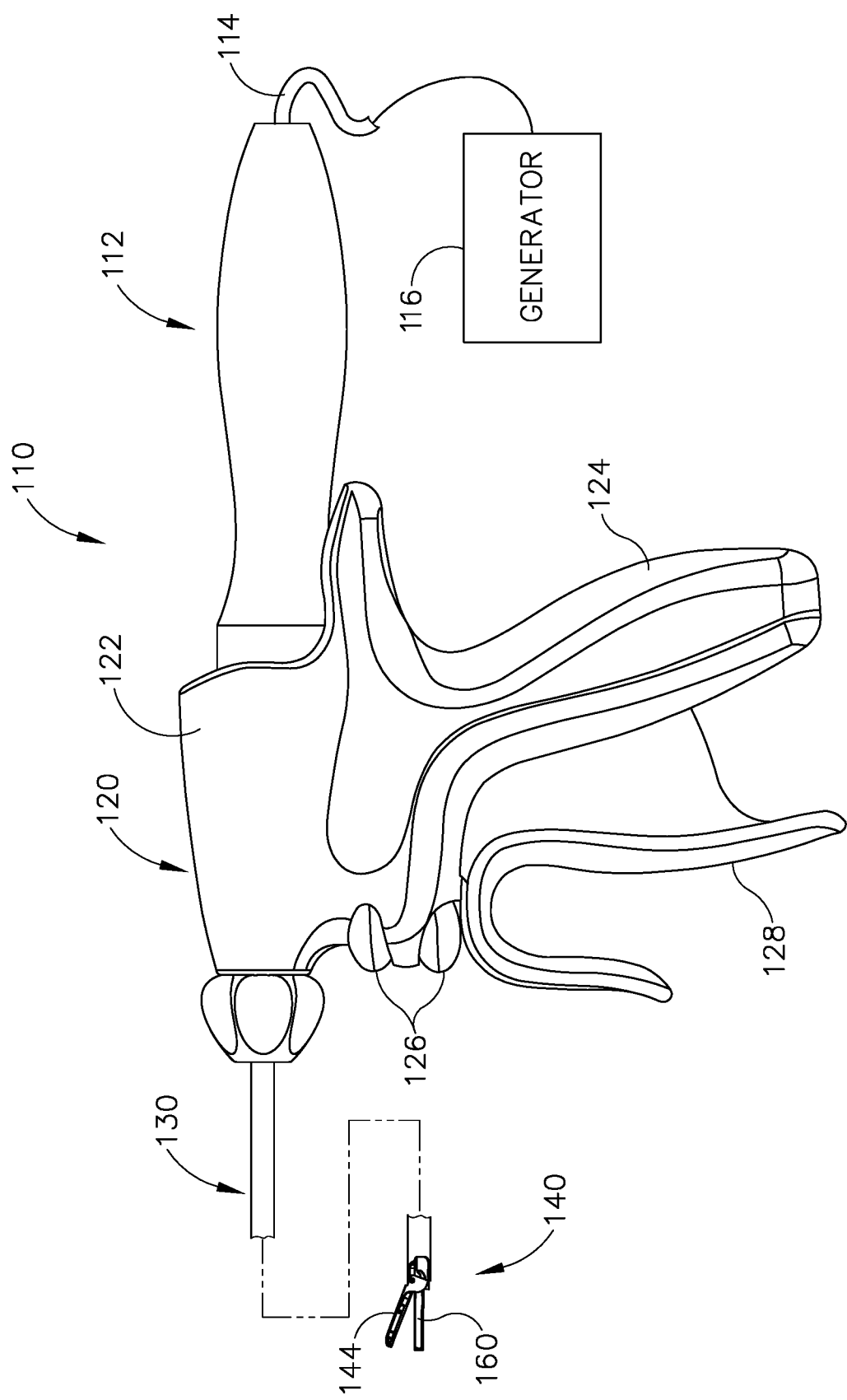
FIG. 2 depicts a side elevational view of an exemplary form that an instrument of the system of FIG. 1 may take.

FIG. 2 illustrates an exemplary ultrasonic surgical instrument (110). At least part of instrument (110) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,203,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (110) is operable to cut tissue and seal or weld tissue substantially simultaneously. It should also be understood that instrument (110) may have various structural and functional similarities with the HARMONIC ACER Ultrasonic Shears, the HARMONIC WAVER Ultrasonic Shears, the HARMONIC FOCUS® Ultrasonic Shears, and/or the HARMONIC SYNERGY® Ultrasonic Blades. Furthermore, instrument (110) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (110), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is pivotably coupled with an inner tube and an outer tube that form shaft assembly (130). Such an inner and outer tube configuration may be provided in accordance with the teachings of various references that are cited herein. Clamp arm (144) is further coupled with trigger (128). Trigger (128) is operable to drive one of the tubes of shaft assembly (130) longitudinally while the other tube of shaft assembly (130) remains stationary. This relative longitudinal movement between the tubes of shaft assembly (130) provides pivotal movement of clamp arm (144). Clamp arm (144) is thus pivotable toward ultrasonic blade (160) in response to pivoting of trigger (128) toward pistol grip (124); and clamp arm (144) is pivotable away from ultrasonic blade (160) in response to pivoting of trigger (128) away from pistol grip (124). Clamp arm (144) is thereby operable to cooperate with ultrasonic blade (160) to grasp and release tissue; and clamp arm (144) is further operable to compress tissue against ultrasonic blade (160) to thereby enhance the communication of ultrasonic vibration from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (136) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (44) and blade (160). In particular, activation of a second one of the buttons (136) may cause vibration of ultrasonic blade (160) at a relatively high amplitude. Other suitable operational modes that may be associated with buttons (126) will be apparent to persons skilled in the art in view of the teachings herein.

III. Exemplary Alternative Surgical Instruments

While instruments such as instrument (110) are effective for cutting and sealing tissue as described above, some instances may call for delivering varying amounts of energy or clamping forces to tissue in order to optimize treatment of the tissue. For example, thicker or denser tissue may require more energy to cut and/or seal than thinner or less dense tissue. Moreover, as tissue being treated changes from an initial, unsealed state to a sealed state, the tissue thickness may decrease, requiring less energy to cut and/or seal as the tissue becomes thinner. In addition to monitoring tissue characteristics, it may be desirable to monitor thermal characteristics of the tissue due to friction between the tissue and the blade (24, 160), in order to prevent an undesired amount heat generation. Various examples of features that may be used to monitor tissue treatment and adjust outputs of instrument (20, 110) are described in greater detail below.

A. Instrument with Sensor to Detect Ultrasonic Blade Deflection

Figure 3:
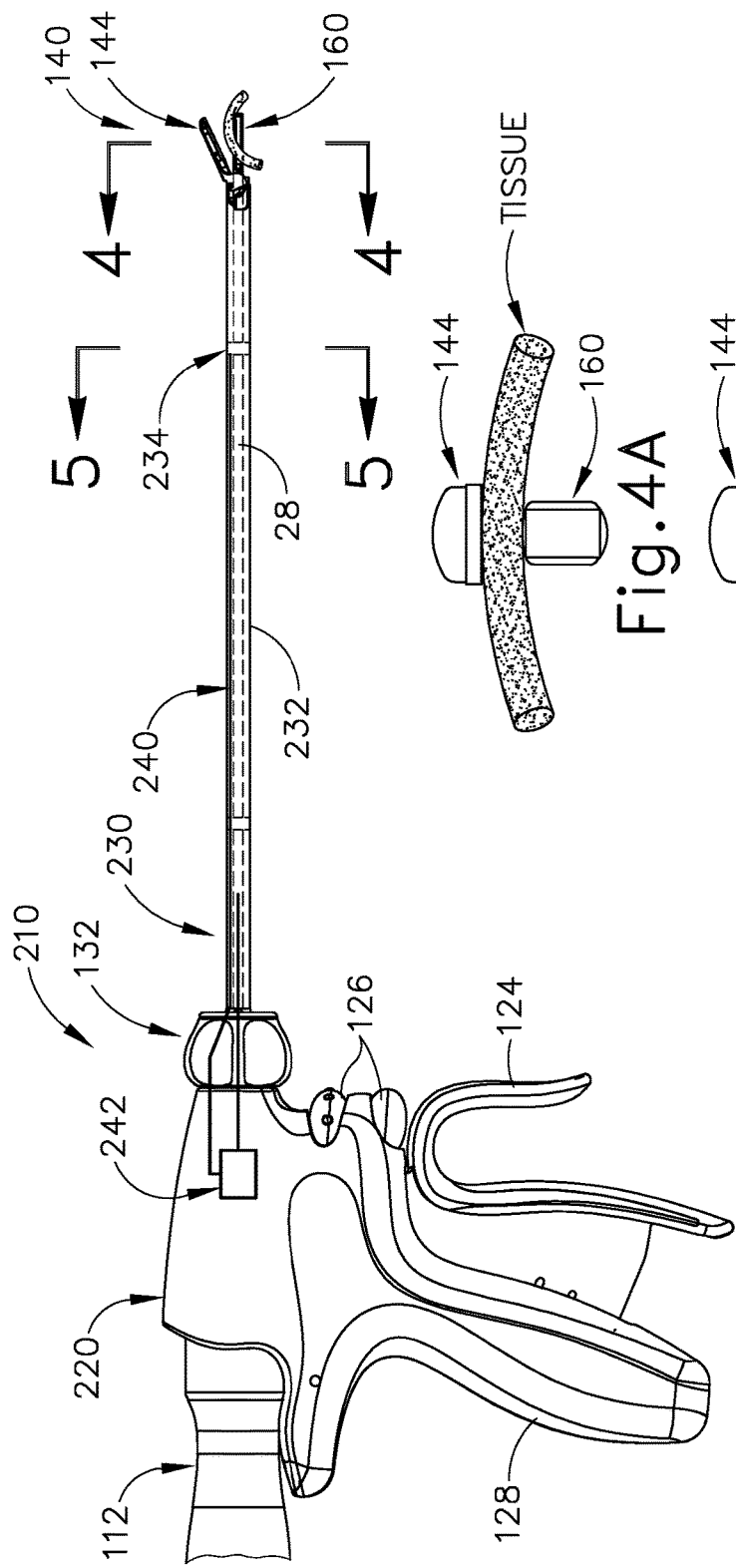
FIG. 3 depicts a side elevational view of an exemplary alternative form that an instrument of the system of FIG. 1 may take.
Figure 4A:
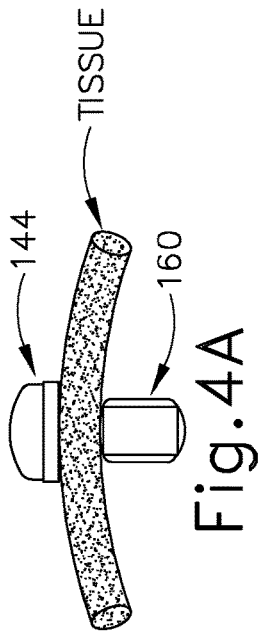
FIG. 4A depicts a cross-sectional view of the instrument of FIG. 3, taken along line 4-4 of FIG. 3, showing an end effector of the instrument in a first partially closed clamping configuration.
Figure 4B:
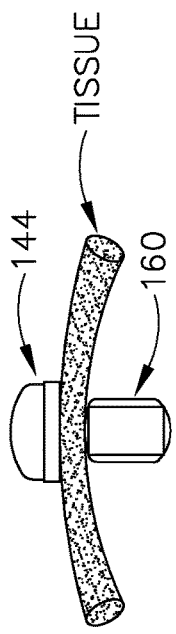
FIG. 4B depicts a cross-sectional view of the instrument of FIG. 3, taken along line 4-4 of FIG. 3, showing the end effector in a second partially closed clamping configuration.
Figure 4C:
FIG. 4C depicts a cross-sectional view of the instrument of FIG. 3, taken along line 4-4 of FIG. 3, showing the end effector in a fully closed clamping configuration.
Figure 5:
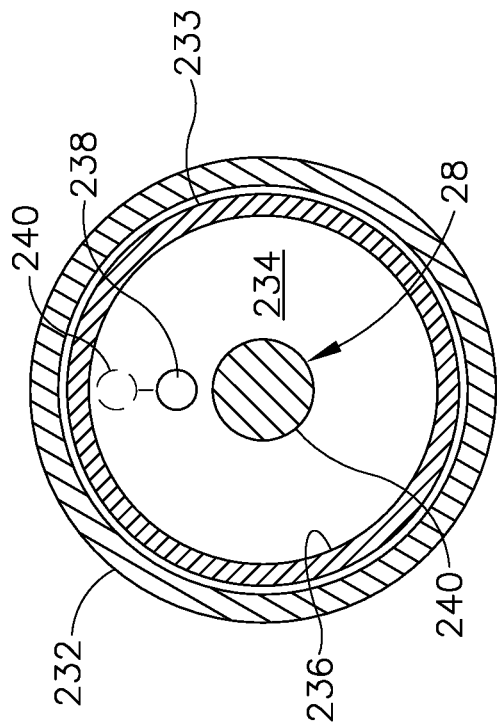
FIG. 5 depicts a cross-sectional view of the instrument of FIG. 3, taken along line 5-5 of FIG. 3.

FIGS. 3-5 show an exemplary alternative instrument (210) that is substantially similar to instrument (110) described above. Therefore, identical or similar structures are labeled with like reference numerals without further explanation below. It should therefore be understood that instrument (210) may be readily incorporated into system (10) as a form of instrument (20). Instrument (210) of this example includes a handle assembly (220) that is just like handle assembly (120) described above. Handle assembly (220) is configured to receive an ultrasonic transducer (112). While not shown in FIG. 3, it should be understood that transducer (112) may be in communication with a generator (12, 116) via cable (14). A shaft assembly (230) extends distally from handle assembly (220). Shaft assembly (230) includes end effector (140) that is configured and operable substantially identically to end effector (140) described above. It should be understood, however, that shaft assembly (230) of this example is not limited to use with end effector (140). By way of example only, shaft assembly (230) may instead be readily combined with end effectors that are operable to apply electrosurgical energy to tissue, end effectors that are operable to apply staples to tissue, end effectors that are operable to apply sutures to tissue, end effectors that are operable to apply clips to tissue, etc.

Shaft assembly (230) is similar to shaft assembly (130) such that it includes an outer tube (232), an inner tube (233) defining a lumen (236), a waveguide (28) coaxially disposed within tubes (232, 233), and a distal seal member (234) sealing off proximal portions of lumen (236). Moreover, as shown best in FIG. 5, distal seal (234) includes a sensor (238) that is operably coupled to the distal seal (234). Because the inner aperture (240) of distal seal (234) is in touching contact with the outer portion (e.g., outer diameter) of waveguide (28), vibrations of waveguide (28) due to oscillation of waveguide (28) will be acoustically and mechanically transferred to distal seal (234) and, thus, sensor (238). In the present example, sensor (238) is embedded in distal seal (234). However, sensor (238) may be coupled to or in communication with distal seal (234) in other suitable ways as will be apparent to persons skilled in the art in view of the teachings herein. In the example shown, sensor (238) is configured to detect levels of lateral deflection of ultrasonic blade (160), from which the sensor (238) may determine the pressure experienced by blade (160) while interacting with tissue. Shaft assembly (230) may be rotated using rotation knob (132).

In the present example, sensor (238) comprises an electroactive material. Various examples of suitable electroactive materials will be apparent to those of ordinary skill in the art in view of the teachings herein. In other examples, sensor (238) may comprise other types of sensors, such as a strain gauge, a piezoelectric sensor, a ferroelectric sensor, pressure sensitive layers of suitable materials such as grapheme, and/or any other suitable kind(s) of sensors. Other suitable forms that sensor (238) may take will be apparent to persons skilled in the art in view of the teachings herein. In the example shown, there is only one sensor (238) of a single type. However, in other examples, there may be multiple sensors (238) of a single type; or multiple sensors (238) of multiple types.

Sensor (238) communicates the sensed deflection and/or pressure to generator (12, 116) via wire (240) to contact ring (242), which is in electrical communication with generator (12, 116). While contact ring (242) is shown to provide electrical communication between wire (240) and generator (12, 116), in other examples, there may be suitable other structures that provide electrical communication between wire (240) and generator (12, 116). In some examples, wire (240) is omitted. In such examples, sensor (238) may communicate the sensed deflection and/or pressure to generator (12, 116) wirelessly using known components and modalities. In some examples, the sensed deflection may be communicated to a controller (not shown) that is located within instrument (210), which then converts the deflection data to a pressure level associated with the deflection data, which then communicates the pressure level to the generator (12, 116).

Generator (12, 116) is configured to deliver a predetermined power profile to instrument (210) based on the pressure level communicated to the generator (12, 116). By way of example, as the tissue is being treated, the tissue state changes from an initial unsealed state (e.g., FIG. 4A) to a coagulated or partially sealed state (e.g., FIG. 4B), to a sealed state (e.g., FIG. 4C), and the tissue thickness decreases through these transitions in tissue state. As the thickness of tissue being clamped between clamp arm (144) and blade (160) decreases, the pressure experienced by blade (160) from tissue decreases, resulting in a decreased deflection of blade (160). The value of the pressure experienced by blade (160) may thus serve as an informational proxy for the state of the tissue. Upon the signal of decreased pressure being communicated to generator (12, 116), generator (12, 116), in some examples, may decrease the power delivered to instrument (210). This may reduce the delivery of ultrasonic power to the tissue by blade (160).

In some examples, changes in the delivered power level may be linearly continuous according to the sensed pressure level. That is, as the sensed pressure level increases or decreases, the level of power delivered to instrument (210) linearly increases or decreases continuously, respectively. Alternatively, the level of power delivered to instrument (210) may be adjusted in a step-wise fashion. Particularly, as the sensed pressure level increases or decreases between threshold pressure levels, the level of power delivered to instrument (210) may increase or decrease, respectively, amongst various discretely stepped levels of power. Moreover, in some examples, generator (12, 116) may cease providing power altogether if it receives a signal indicative of a pressure level associated with tissue that is in a sealed, cut and sealed, or other state where it is desirable to cease provision of power. Such power levels and settings associated with particular sensed pressure levels may be stored on a memory of generator (12, 116).

In the example shown, generator (12, 116) or instrument (210) may communicate to the operator the state of the tissue based on the sensed pressure level. For example, generator (12, 116) or instrument (210) may provide an indication to the operator that, based on the sensed pressure level, the tissue is in the initial state, a partially sealed state, a sealed state, a cut and sealed state, or another tissue state that will be apparent to persons skilled in the art in view of the teachings herein. The indication to the operator may be visual, audio, physical (e.g., haptic), any other suitable indication modes, or combinations thereof.

B. Surgical Instrument Including Pressure Sensor for Sensing Clamp Force

FIGS. 6-8 show an exemplary alternative instrument (310) that is configured to operate substantially similar to surgical instrument (110). Therefore, identical or similar structures are labeled with like reference numerals without further explanation below. It should be understood that instrument (310) may be readily incorporated into system (10) as a form of instrument (20). While an end effector is not shown in FIG. 6, instrument (310) includes an end effector that is just like end effector (140) described above. As discussed in further detail below, instrument (310) is configured to sense different characteristics associated with clamping tissue being clamped by end effector (140); and is configured to deliver a particular amount of power to ultrasonic blade (160) based on the sensed characteristics.

As shown, instrument (310) includes a handle assembly (320) that is just like handle assembly (120) described above. Particularly, handle assembly (320) includes pistol grip (128), trigger (124), and a series of links (322a, 322b) that are operably coupled to trigger (124). Links (322a, 322b) operably couple trigger (124) to clamp arm (144) such that clamp arm (144) will pivot in response to pivotal movement of trigger (124) relative to pistol grip (128). Handle assembly (320) also includes an actuating ring (324) that is coupled to link (322b). A linear driver (328) is coaxially positioned within actuating ring (324) and is operable to translate longitudinally relative to handle assembly (320). The distal end of linear driver (328) is pivotably coupled with clamp arm (144), such that longitudinal translation of linear driver (328) provides pivotal movement of clamp arm (144) toward and away from blade (160). The proximal end of linear driver (328) includes an integral, outwardly extending flange (327). In some versions, linear driver (328) comprises an inner tube or an outer tube that forms part of shaft assembly (130). A spring stack (326) is positioned between actuating ring (324) and flange (327). As will be described in greater detail below, spring stack (326) is operable to communicate longitudinal translation of actuating ring (324) to flange (327), and thereby translate linear driver (328), up to a predetermined force threshold.

The distal end of link (322a) is pivotably coupled to trigger (124) at pivot point (330), while the proximal end of link (322a) is coupled to the proximal end of link (322b). Actuating ring (324) is secured to the distal end of link (322b). In the present example, a spring (329) biases link (322b) in the distal direction, thereby biasing actuating ring (324) in the distal direction. In the present example, spring (329) comprises a coil tension spring, but in other examples may comprise any suitable type of resilient member. It should be understood that, due to the couplings between trigger (124), link (322a, 322b), actuating ring (324), and link system (328), actuation of trigger (124) with a sufficient force to overcome the bias of spring (329) results in proximal translation of actuating ring (324). Similarly, releasing the sufficient force on trigger (124) causes actuating ring (324) to return to the distal position in response to the resilient bias of spring (329).

As noted above, spring stack (326) is operable to communicate longitudinal translation of actuating ring (324) to flange (327), and thereby translate linear driver (328), up to a predetermined force threshold, such that spring stack (326) acts as a force limiter with respect to transmission of forces from actuating ring (324) to flange (327). In other words, spring stack (326) is configured to restrict the amount of clamping force that can be transferred to clamp arm (144) in response to pivotal movement of trigger (124) toward pistol grip (128). In the present example, spring stack (326) comprises a coaxially aligned stack of wave springs. However, in other examples, spring stack (326) may comprise any suitable type of resilient member(s) and arrangement.

In addition to overcoming the biasing force of spring (329) to pivot clamp arm (144) toward blade (160), clamp arm (144) also encounters resistance against closing or pivoting toward blade (160) from tissue, particularly during the clamping of tissue between clamp arm (144) and blade (160). Clamp arm (144) may thus provide some degree of mechanical resistance to a clamping action as clamp arm (144) compresses tissue against blade (160). Spring stack (326) has sufficient rigidity to fully transfer linear movement of actuating ring (324) to flange (327) when clamp arm (144) provides mechanical resistance up to a certain predetermined threshold. Spring stack (326) does not compress when the mechanical resistance is below this threshold. However, when clamp arm (144) provides mechanical resistance beyond the threshold, spring stack (326) will begin to compress, such that further pivotal movement of trigger (124) will result in further proximal movement of actuating ring (324) without resulting in further proximal movement of flange (324) or linear driver (328). This compression of spring stack (326) may prevent undue damage to components of instrument (310) and/or undue damage to tissue that is being compressed by end effector (140). Various suitable force thresholds that may be provided through spring stack (326) will be apparent to those of ordinary skill in the art in view of the teachings herein.

Instrument (310) of the present example further includes a plurality of sensors (340, 342, 344, 346) that are configured to sense the clamping force experienced by clamp arm (144) during the clamping of tissue. In the example shown, sensors (340, 342, 344, 346) are each pressure sensors, but in other examples, one or more of sensors may be other suitable types of sensors which will be apparent to persons skilled in the art in view of the teachings herein. As shown, there are four sensors (340, 342, 344, 346), but it will be understood that there may be less than four sensors (340, 342, 344, 346), such as one, two, or three sensors, or more than four sensors. For example, there may be only one sensor operably coupled to spring stack (326) (e.g., sensor (340)).

In the present example, sensor (340) is positioned on actuating ring (324) such that sensor (340) contacts a distal portion (348) of spring stack (326). Sensor (342) is positioned on flange (327) such that sensor (342) contacts a proximal portion (350) of spring stack (326). Therefore, as actuating ring (324) is urged proximally in response to actuation of trigger (124), sensors (340, 342) experience the forces and/or pressure from actuating ring (324) on spring stack (326), and between spring stack (326) and flange (327), respectively. Sensor (344) is positioned on proximal end of link (322b), distally of spring (329), while sensor (346) is positioned distally of spring (329) and is coupled to the housing of handle assembly (320). Therefore, as link (322b) is moves proximally in response to trigger (124) being actuated, sensors (344, 346) are subjected to the forces from link (322b) onto spring (329) and from the housing of handle assembly (320) onto spring (329). Other suitable configurations and positions of sensors (340, 342, 344, 346) will be apparent to persons skilled in the art in view of the teachings herein.

Instrument (310) is configured to deliver an amount of energy to waveguide (28), and thus blade (160), based on the sensed clamping force by one or more of sensors (340, 342, 344, 346). Particularly, in the present example, generator (12, 116) is configured to deliver a predetermined power profile to instrument (310) based on the pressure level communicated to generator (12, 116). When a lower pressure level is sensed by one or more of sensors (340, 342, 344, 346), generator (12, 116) delivers a "low" level of power, thereby causing blade (160) to vibrate at a relatively low level of ultrasonic power. Similarly, when a higher pressure level is sensed by one or more of sensors (240, 242, 244, 246), generator (12, 116) delivers a "high" level of power, thereby causing blade (160) to vibrate at a relatively high level of ultrasonic power. Suitable amounts of power that are associated with the "high" and low" levels will be apparent to persons skilled in the art in view of the teachings herein.

As discussed above, as the tissue is being treated, the tissue state changes from an initial unsealed state (e.g., FIG. 4A) to a coagulated or partially sealed state (e.g., FIG. 4B), to a sealed state (e.g., FIG. 4C), and the tissue thickness decreases through these transitions. As the tissue thickness being clamped between clamp arm (144) and blade (160) decreases, the required clamping force on tissue decreases and thus the pressure level read by sensors (340, 342, 344, 346) may decrease in some examples. Upon the signal of decreased pressure being communicated to generator (12, 116), generator (12, 116) may decrease the power delivered to instrument (310). In some examples, changes in the delivered power level may be linearly continuous according to the sensed pressure level. That is, as the sensed pressure level increases or decreases, the level of power delivered to instrument (310) linearly increases or decreases continuously, respectively. Alternatively, the level of power delivered to instrument (310) may be adjusted in a step-wise fashion. Particularly, as the sensed pressure level increases or decreases between threshold pressure levels, the level of power delivered to instrument (310) may increase or decrease, respectively, amongst various discretely stepped levels of power. Moreover, in some examples, generator (12, 116) may cease providing power altogether if it receives a signal indicative of a pressure level associated with tissue that is in a sealed, cut and sealed, or other state where it is desirable to cease provision of power. Such power levels and settings associated with particular sensed pressure levels may be stored on a memory of generator (12, 116).

It will be understood that in addition to, or in lieu of, changing the power output to alter the amount of energy delivered and (thus the heat generated due to friction), the clamp force of clamp arm (144) may be adjusted. This is because, as it will be understood by persons skilled in the art, heat generation due to friction is defined by the equation $Q = \mu \times V \times F$, where $\mu$ is the kinetic coefficient of friction, V is the relative velocity between the surfaces, and F is the normal source. Thus, rather than decreasing or increasing V by decreasing or increasing the power output to blade (160), respectively, the normal force (i.e., the clamping force) may be decreased or increased. For example, as the tissue thickness decreases, it may be desirable to decrease the clamp force in order to decrease heat generation and, in some cases, to prevent cutting the tissue, such as in instances where only sealing is desired. However, it may be desirable to do so without fully relying on the skill of the operator or tactile, visual, or other feedback provided to the operator during an operation.

As shown in FIG. 7, instrument (310) includes a spring compression mechanism (360) that is operably coupled to spring stack (326). In the example shown, spring compression mechanism (360) is operable to adjust the pre-load of spring stack (326). By adjusting the pre-load of spring stack (326), spring compression mechanism (360) is operable to adjust the mechanical resistance threshold provided by spring stack (326). In other words, spring compression mechanism (360) is operable to adjust the point at which spring stack (326) transitions from a full transmission state (i.e., where spring stack (326) provides full transmission of proximal movement of actuating ring (324) to flange (327)) to a non-transmission state (i.e., where spring stack (326) compresses in response to proximal movement of actuating ring (324), without transmitting proximal movement to flange (327)). This may in turn effectively decrease the clamping force of clamp arm (144) resulting from an actuation of trigger (124). Similarly, spring compression mechanism (360) is operable to increase the pre-load of spring stack (326), thereby increasing the clamping force of clamp arm (144) resulting from an actuation of trigger (124). It will be understood that changing the pre-load of spring stack (326), trigger (124) may be actuated with the same sufficient force, but such actuation under different levels of pre-loads results in different clamping forces that clamp arm (144) may provide.

In the present example, one of sensors (340, 342, 344, 346) may be configured to detect frequency slope. In other examples, instrument (310) may include an additional sensor or sensors that are configured to detect frequency slope during operation of instrument (310). In either context, spring compression mechanism (360) may be configured to automatically increase or decrease the pre-load on spring stack (326) based on the frequency slope detection of one of sensors (340, 342, 344, 346). In addition or in the alternative, spring compression mechanism (360) may be configured to automatically increase or decrease the pre-load on spring stack (326) based on sensed pressure data from one or more of sensors (340, 342, 344, 346). In addition or in the alternative, spring compression mechanism (360) may be operably coupled with other sensors, such as temperature sensors or other types of sensors (e.g., positioned on shaft assembly (130) and/or end effector (140)), which may further influence spring compression mechanism (360) automatically increasing or decreasing the pre-load on spring stack (326).

Figure 9:
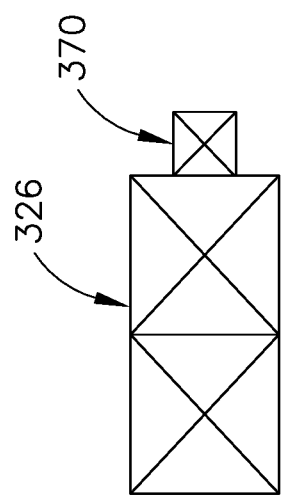
FIG. 9 depicts an exemplary spring compression mechanism that may be incorporated into the instrument of FIG. 6.

In the example shown in FIG. 9, spring compression mechanism (360) comprises a solenoid (370) that is configured to adjust the pre-load of spring stack (326) in response to data sensed by one of sensors (320, 322, 324, 326). In such examples, solenoid (370) may be operable to compress spring stack (326) among discrete levels of pre-load, and thus change the clamping force of clamp arm (144) among discrete clamp force amounts. Suitable configurations of solenoid (370) will be apparent to persons skilled in the art in view of the teachings herein. In other examples, the increasing or decreasing of clamping force based on the adjustment of solenoid may be linearly continuous.

Figure 10:
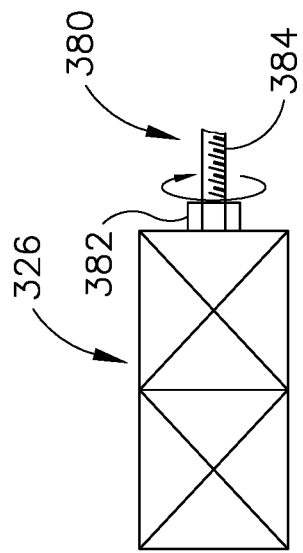
FIG. 10 depicts an exemplary alternative spring compression mechanism that may be incorporated into the instrument of FIG. 6.

In the example shown in FIG. 10, spring compression mechanism (360) comprises a torsional nut driven adjustment system (380) including a nut (382) threaded around a threaded rod (384). In such examples, nut (382) may be rotated in one direction to increase the pre-load; and in a second, opposite direction to decrease the pre-load, in response to the sensed data. Other configurations of spring compression mechanism (360) that are suitable to increase and decrease the pre-load on spring stack (326) will be apparent to persons skilled in the art in view of the teachings herein. It should also be understood that spring compression mechanism (360) may be used in addition to, or in lieu of, adjusting the power output to blade (160) based on force data from sensors (320, 322, 324, 326).

C. Instrument with User Adjustable Clamp Force

FIGS. 11-12 show an exemplary alternative instrument (410) that is configured to operate substantially similar to surgical instrument (110). Therefore, identical or similar structures are labeled with like reference numerals without further explanation below. It should be understood that instrument (410) may be readily incorporated into system (10) as a form of instrument (20). While an end effector is not shown in FIG. 11, instrument (410) includes an end effector that is just like end effector (140) described above. Moreover, instrument (410) includes a handle assembly (420) that is just like handle assembly (320) described above, except that in the example shown, certain elements, such as sensors (340, 342, 344, 346), are omitted. However, it will be understood that such elements and their functionality may be incorporated into instrument (410) if desired.

Instrument (410) includes a toggle switch (460) that is operably coupled to spring stack (326) in order to change the pre-load of spring stack (326). That is, spring toggle switch (460) is operable to decrease the pre-load on spring stack (326), thus decreasing the effective clamping force of clamp arm (144) resulting from actuation of trigger (124). Similarly, toggle switch (460) is operable to increase the pre-load on spring stack (326), thus increasing the effective clamping force of clamp arm (144) resulting from actuation of trigger (124). Particularly, as shown, the operator may toggle the toggle switch (460) from a first position (adjacent to the "−" symbol) to a second position (adjacent to the "+" symbol), or to positions between the first and second positions.

In the example shown, toggle switch (460) pivots about an axis between the first and second positions, but in other examples may move axially or in other suitable manners. In the example shown, the first position is associated with a "low" setting or clamp force while the second position is associated with a "high" setting or clamp force of clamp arm (144). Positions of toggle switch (460) between the first and second positions are associated with a setting between the "low" and "high" settings. Therefore, as the operator toggles the toggle switch (460) clockwise between the first and second positions, the pre-load of spring stack (326) increases, while toggling switch (460) in a counterclockwise direction results in the pre-load of spring stack (326) decreasing. Suitable amounts of clamp force associated with the "high," "low" and other settings of clamp force will be apparent to persons skilled in the art in view of the teachings herein.

Thus, toggle switch (460) provides an operator with the ability to adjust the clamp force of end effector (140). In some examples, spring stack (326) may move among discrete levels of pre-load in response to toggling of toggle switch (460), and thus change the clamping force of clamp arm (144) among discrete clamp force amounts. However, in other examples, the increasing or decreasing of clamping force based on the adjustment of toggle switch (460) may be linearly continuous. Other suitable configurations of toggle switch (460) will be apparent to persons skilled in the art in view of the teachings herein. Similarly, various suitable structures that may be coupled between toggle switch (460) and spring stack (326) in order to provide the adjustable pre-load and clamping force will be apparent to those of ordinary skill in the art in view of the teachings herein.

In some examples, switch (460) may be used in conjunction with an adjustable amplitude switch that automatically or manually adjusts the power delivered to blade (160) based on the position of toggle switch (460). The power may be adjusted manually or automatically (e.g., in response to input from sensors like sensors (340, 342, 344, 346)) or based upon the position of toggle switch (460). In some examples, toggle switch (460) may be selectively disengageable from shaft assembly (130) in order to enable rotation of components of shaft assembly (130).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body; (b) a shaft assembly extending distally from the body, wherein the shaft assembly comprises an acoustic waveguide; (c) an end effector comprising an ultrasonic blade, wherein the ultrasonic blade is in acoustic communication with the acoustic waveguide; and (e) a sensor configured to sense at least one characteristic of the shaft assembly and/or the end effector, wherein the end effector is configured to be activated at varying ultrasonic power levels based on the at least one characteristic sensed by the sensor.

Example 2

The ultrasonic instrument of claim 1, wherein the shaft assembly comprises a distal seal, wherein the acoustic waveguide is in communication with the distal seal.

Example 3

The ultrasonic instrument of claim 2, wherein the sensor is positioned on the distal seal, wherein the sensor is configured to sense the forces on the distal seal in response to oscillation of the ultrasonic waveguide.

Example 4

The ultrasonic waveguide of claim 3, wherein the sensor comprises an electroactive material.

Example 5

The ultrasonic waveguide of claim 3, wherein the sensor comprises a piezoelectric component.

Example 6

The ultrasonic waveguide of claim 3, wherein the sensor comprises a strain gauge.

Example 7

The ultrasonic waveguide of claim 3, wherein the sensor comprises a ferroelectric element.

Example 8

The ultrasonic waveguide of claim 1, wherein the sensor is positioned in the body.

Example 9

The ultrasonic instrument of claim 1, wherein the end effector comprises a clamp arm, wherein the clamp arm is pivotable toward and away from the ultrasonic blade in order to clamp tissue between the clamp arm and ultrasonic blade, wherein the at least one characteristic comprises a clamp force of the clamp arm onto tissue clamped between the clamp arm and the ultrasonic blade.

Example 10

The ultrasonic instrument of claim 9, wherein the body comprises a spring element, wherein the spring element is configured to bias the clamp arm in the open position.

Example 11

The ultrasonic instrument of claim 10, wherein the sensor is positioned to contact the spring element.

Example 12

The ultrasonic instrument of claim 11, wherein the body further comprises a trigger, wherein the clamp arm is configured to pivot toward the ultrasonic blade in response to actuation of the trigger, wherein the spring element is configured to be compressed in response to actuation of the trigger.

Example 13

The ultrasonic instrument of claim 12, wherein the sensor is configured to remain in contact with the spring element as the spring element is compressed.

Example 14

The ultrasonic instrument of claim 11, wherein the sensor comprises a pressure sensor.

Example 15

The ultrasonic instrument of claim 1, further comprising a generator, wherein the sensor is in communication with the generator, wherein the generator is configured to deliver power to the ultrasonic instrument in response to an input from the sensor.

Example 16

The ultrasonic instrument of claim 15, wherein the sensor is configured to wirelessly transmit information to the generator.

Example 17

An ultrasonic instrument comprising: (a) a body; (b) a shaft assembly extending distally from the body, wherein the shaft assembly comprises an acoustic waveguide; (c) an end effector, comprising: (i) an ultrasonic blade, wherein the ultrasonic blade is in acoustic communication with the acoustic waveguide, and (ii) a clamp arm, wherein the clamp arm is pivotable toward and away from the ultrasonic blade in order to clamp tissue between the end effector and ultrasonic blade; and (d) a toggle switch, wherein the toggle switch is configured to adjust a level of clamp force associated with the clamp arm upon movement of the toggle switch.

Example 18

The ultrasonic instrument of claim 17, wherein the toggle switch is positioned on the body.

Example 19

The ultrasonic instrument of claim 18, wherein the acoustic waveguide is configured to be activated at a predetermined power level based on the position of the toggle switch.

Example 20

An ultrasonic instrument comprising: (a) a body; (b) a shaft assembly extending distally from the body, wherein the shaft assembly comprises an acoustic waveguide; (c) an end effector, comprising: (i) an ultrasonic blade, wherein the ultrasonic blade is in acoustic communication with the acoustic waveguide, and (ii) a clamp arm, wherein the clamp arm is pivotable toward and away from the ultrasonic blade in order to clamp tissue between the end effector and ultrasonic blade; and (d) a sensor, wherein the sensor is not positioned on the end effector, wherein the sensor is configured to sense a clamp force associated with the clamp arm.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) a shaft assembly including an acoustic waveguide;
   (b) an end effector distally extending from the shaft assembly, including:
      (i) an ultrasonic blade in acoustic communication with the acoustic waveguide, and
      (ii) a clamp arm movably secured relative to the ultrasonic blade and configured to move from an open position toward a closed position, wherein the clamp arm is further configured to compress tissue against the ultrasonic blade with a clamp force while moving the clamp arm toward the closed position;
   (c) a drive member operatively connected to the clamp arm and configured to selectively actuate from a first position toward a second position to thereby respectively direct the clamp arm from the open position toward the closed position;

(d) a force limiter operatively connected between the drive member and the clamp arm, wherein the force limiter is configured to transfer movement from the drive member toward the clamp arm and limit force transferred therethrough to a first adjusted clamp force or a second adjusted clamp force for restricting the clamp force at the clamp arm respectively according to the first or second adjusted clamp force, wherein the force limiter is configured to be selectable between the first adjusted clamp force and the second adjusted clamp force by an operator; and (e) a linear driver positioned along the shaft assembly and in contact with the force limiter, wherein the linear driver is configured to transfer movement from the force limiter toward the clamp arm, wherein the linear driver includes a flange positioned proximal to the force limiter.

2. The ultrasonic surgical instrument of claim 1, wherein at least a portion of the force limiter is selectively movable from a first position to a second position, wherein the at least the portion of the force limiter in the first position is configured to limit force to the first adjusted clamp force for restricting the clamp force at the clamp arm, and wherein the at least the portion of the force limiter in the second position is configured to limit force to the second adjusted clamp force for restricting the clamp force at the clamp arm.

3. The ultrasonic surgical instrument of claim 2, wherein the at least the portion of the force limiter includes a switch, wherein the switch is selectively movable from the first position to the second position.

4. The ultrasonic surgical instrument of claim 3, wherein the switch is a toggle switch configured to toggle between the first position and the second position.

5. The ultrasonic surgical instrument of claim 4, wherein the force limiter further includes a resilient biasing feature, wherein the resilient biasing feature is operatively connected to the clamp arm such that the clamp arm is resiliently biasedly mounted relative to the ultrasonic blade.

6. The ultrasonic surgical instrument of claim 1, further comprising a body, wherein the shaft assembly distally extends from the body.

7. The ultrasonic surgical instrument of claim 6, wherein the shaft assembly is configured to selectively rotate relative to the body.

8. The ultrasonic surgical instrument of claim 7, wherein at least a portion of the force limiter is selectively movable from a first engaged position to a disengaged position.

9. The ultrasonic surgical instrument of claim 8, wherein the at least the portion of the force limiter includes a switch, wherein the switch is selectively movable to the first engaged position, a second engaged position, and the disengaged position, wherein the switch in the first engaged position is configured to limit force to the first adjusted clamp force for restricting the clamp force at the clamp arm, and wherein the switch in the second engaged position is configured to limit force to the second adjusted clamp force for restricting the clamp force at the clamp arm.

10. The ultrasonic surgical instrument of claim 9, wherein the switch is a toggle switch configured to toggle between the first engaged position, the second engaged position, and the disengaged position.

11. The ultrasonic surgical instrument of claim 1, wherein the force limiter further includes:

(i) a resilient biasing feature operatively connected to the clamp arm such that the clamp arm is resiliently biasedly mounted relative to the ultrasonic blade with at least one of a first pre-load or a second pre-load, and (ii) a switch selectively movable from a first position to a second position, wherein the switch in the first position directs the resilient biasing feature to the first pre-load to thereby limit force to the first adjusted clamp force for restricting the clamp force at the clamp arm, and wherein the switch in the second position directs the resilient biasing feature to the second pre-load to thereby limit force to the second adjusted clamp force for restricting the clamp force at the clamp arm.

12. The ultrasonic surgical instrument of claim 11, wherein the first pre-load is a lower pre-load such that the first adjusted clamp force is a lower adjusted clamp force, and wherein the second pre-load is a higher pre-load such that the second adjusted clamp force is a higher adjusted clamp force.

13. The ultrasonic surgical instrument of claim 12, wherein the force limiter further includes an actuating member operatively connected to the drive member, wherein the resilient biasing feature is positioned in compression between the actuating member and the switch, and wherein the drive member is configured to move toward the switch and further compress the resilient biasing feature as the drive member is selectively moved from the first position toward the second position.

14. A method of limiting a clamp force of an ultrasonic surgical instrument, the ultrasonic surgical instrument including (a) a shaft assembly including an acoustic waveguide; (b) an end effector distally extending from the shaft assembly, including: (i) an ultrasonic blade in acoustic communication with the acoustic waveguide, and (ii) a clamp arm movably secured relative to the ultrasonic blade and configured to move from an open position toward a closed position, wherein the clamp arm is further configured to compress tissue against the ultrasonic blade with the clamp force while moving the clamp arm toward the closed position; (c) a drive member operatively connected to the clamp arm and configured to selectively actuate from a first position toward a second position to thereby respectively direct the clamp arm from the open position toward the closed position; (d) a force limiter operatively connected between the drive member and the clamp arm, wherein the force limiter is configured to transfer movement from the drive member toward the clamp arm and limit force transferred therethrough to a first adjusted clamp force or a second adjusted clamp force for restricting the clamp force at the clamp arm respectively according to the first or second adjusted clamp force, wherein the force limiter is configured to be selectable between the first adjusted clamp force and the second adjusted clamp force by an operator; and (e) a linear driver positioned along the shaft assembly and in contact with the force limiter, wherein the linear driver is configured to transfer movement from the force limiter toward the clamp arm, wherein the linear driver includes a flange positioned proximal to the force limiter, the method comprising:

(a) selectively transferring movement from at least a portion of the force limiter to the clamp arm via the linear driver to thereby adjust the clamp force from the first adjusted clamp force to the second adjusted clamp force and limit the clamp force applied via the clamp arm to the second adjusted clamp force.

15. The method of claim 14, wherein the at least the portion of the force limiter includes a switch.

16. The method of claim 15, wherein the force limiter further includes a resilient biasing feature, and wherein the method further comprises selectively urging the drive member from the first position toward the second position to thereby compress the resilient biasing feature and move the clamp arm from the open position toward the closed position.

* * * * *